(12) United States Patent
Wu (10) Patent No.: US 9,138,592 B2
(45) Date of Patent: Sep. 22, 2015

(54) DEFIBRILLATION SYSTEM AND METHOD AND DEFIBRILLATOR ELECTRODE DEVICE

(71) Applicant: THINKCLOUD DIGITAL TECHNOLOGY CO., LTD., Taichung (TW)

(72) Inventor: Yu-Jen Wu, Taichung (TW)

(73) Assignee: THINKCLOUD DIGITAL TECHNOLOGY CO., LTD., Taichung (TW)

( * ) Notice: Subject to any disclaimer, the term of this patent is extended or adjusted under 35 U.S.C. 154(b) by 62 days.

(21) Appl. No.: 14/074,717

(22) Filed: Nov. 8, 2013

(65) Prior Publication Data
US 2014/0324111 A1    Oct. 30, 2014

(30) Foreign Application Priority Data
Apr. 29, 2013   (TW) .............................. 102115284 A (51) Int. Cl.
*A61N 1/00*      (2006.01)
*A61N 1/39*      (2006.01)

(52) U.S. Cl.
CPC ............ *A61N 1/3993* (2013.01); *A61N 1/3968* (2013.01)

(58) Field of Classification Search
CPC ........................... A61N 1/3968; A61N 1/3993
See application file for complete search history.

(56) References Cited

U.S. PATENT DOCUMENTS

| | | | |
|---|---|---|---|
| 8,838,235 B2 * | 9/2014 | Cowan et al. | 607/5 |
| 2008/0001735 A1 | 1/2008 | Tran | |
| 2010/0042171 A1 | 2/2010 | Saketkhou | |
| 2011/0022105 A9 | 1/2011 | Owen et al. | |
| 2013/0304147 A1 * | 11/2013 | Aoyama et al. | 607/6 |

OTHER PUBLICATIONS

Search Report of TW Patent Application No. 102115284 dated Dec. 11, 2014, with English translation (3 pages).

* cited by examiner

*Primary Examiner* — George Manuel
(74) *Attorney, Agent, or Firm* — DLA Piper LLP (US)

(57) ABSTRACT

A defibrillation system includes an electrode set to contact a biological subject, and a portable electronic device supporting mobile wireless communications and coupled to the electrode set. The portable electronic device includes a processor and a memory unit. The memory unit stores program instructions which, when executed by the processor, enables the processor to obtain an electro-cardiac signal of the biological subject through the electrode set, and output a discharge command according to the electro-cardiac signal for delivering an electrical shock to the biological subject through the electrode set.

14 Claims, 10 Drawing Sheets

DEFIBRILLATION SYSTEM AND METHOD AND DEFIBRILLATOR ELECTRODE DEVICE

CROSS-REFERENCE TO RELATED APPLICATION

This application claims priority to Taiwanese Application No. 102115284, filed on Apr. 29, 2013.

BACKGROUND OF THE INVENTION

1. Field of the Invention

The invention relates to a defibrillation system, and more particularly to a defibrillation system including a portable electronic device that supports mobile wireless communications.

2. Description of the Related Art

Ventricular tachycardia (VT) and ventricular fibrillation (VF) may result in cardiogenic sudden death within a few minutes if first aid is not immediately provided.

Defibrillation is an effective treatment for pulseless VT and VF. Automatic external defibrillators (AEDs) are commonly found in public places in some countries, such as the United States, the United Kingdom and Japan, thereby promoting survival rate of cardiac dysrhythmia.

However, while people may suffer from VT/VF anywhere, the AEDs are only disposed at crowded places.

SUMMARY OF THE INVENTION

Therefore, an object of the present invention is to provide a portable defibrillation system that may be used at any time as required.

According to one aspect of the present invention, a defibrillation system comprises:

an electrode set adapted to contact a biological subject; and a portable electronic device that supports mobile wireless communications, that is coupled electrically and separably to the electrode set, and that includes a processor and a memory unit coupled to the processor.

The memory unit stores program instructions which, when executed by the processor, enables the processor to obtain an electro-cardiac signal of the biological subject through the electrode set that contacts the biological subject, and output a discharge command according to the electro-cardiac signal for delivering an electrical shock to the biological subject, the electrical shock being delivered through the electrode set according to the discharge command.

Another object of the present invention is to provide a defibrillator electrode device adapted for use with a portable electronic device that supports mobile wireless communications and that includes a processor.

According to another aspect of the present invention, a defibrillator electrode device comprises:

an electrode set adapted to contact a biological subject; and program instructions to be stored in the portable electronic device, the program instructions, when executed by the processor of the portable electronic device, enabling the processor to obtain an electro-cardiac signal of the biological subject through the electrode set that contacts the biological subject, and output a discharge command according to the electro-cardiac signal for delivering an electrical shock to the biological subject, the electrical shock being delivered through the electrode set according to the discharge command.

Yet another object of the present invention is to provide a defibrillation method.

According to yet another aspect of the present invention, a defibrillation method comprises:

connecting an electrode set to a portable electronic device that supports mobile wireless communications, the electrode set configured to contact a biological subject;

obtaining, using a processor of the portable electronic device, an electro-cardiac signal of the biological subject through the electrode set; and outputting, using the processor of the portable electronic device, a discharge command according to the electro-cardiac signal for delivering an electrical shock to the biological subject, the electrical shock being delivered through the electrode set according to the discharge command.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Referring to FIGS. 1 to 4, a first preferred embodiment of the defibrillation system according to this invention is shown to include a voltage transformer 1, an electrode set 2 to contact a biological subject, and a portable electronic device 3 that supports mobile wireless communications. In this embodiment, the biological subject is a human subject.

Figure 1:
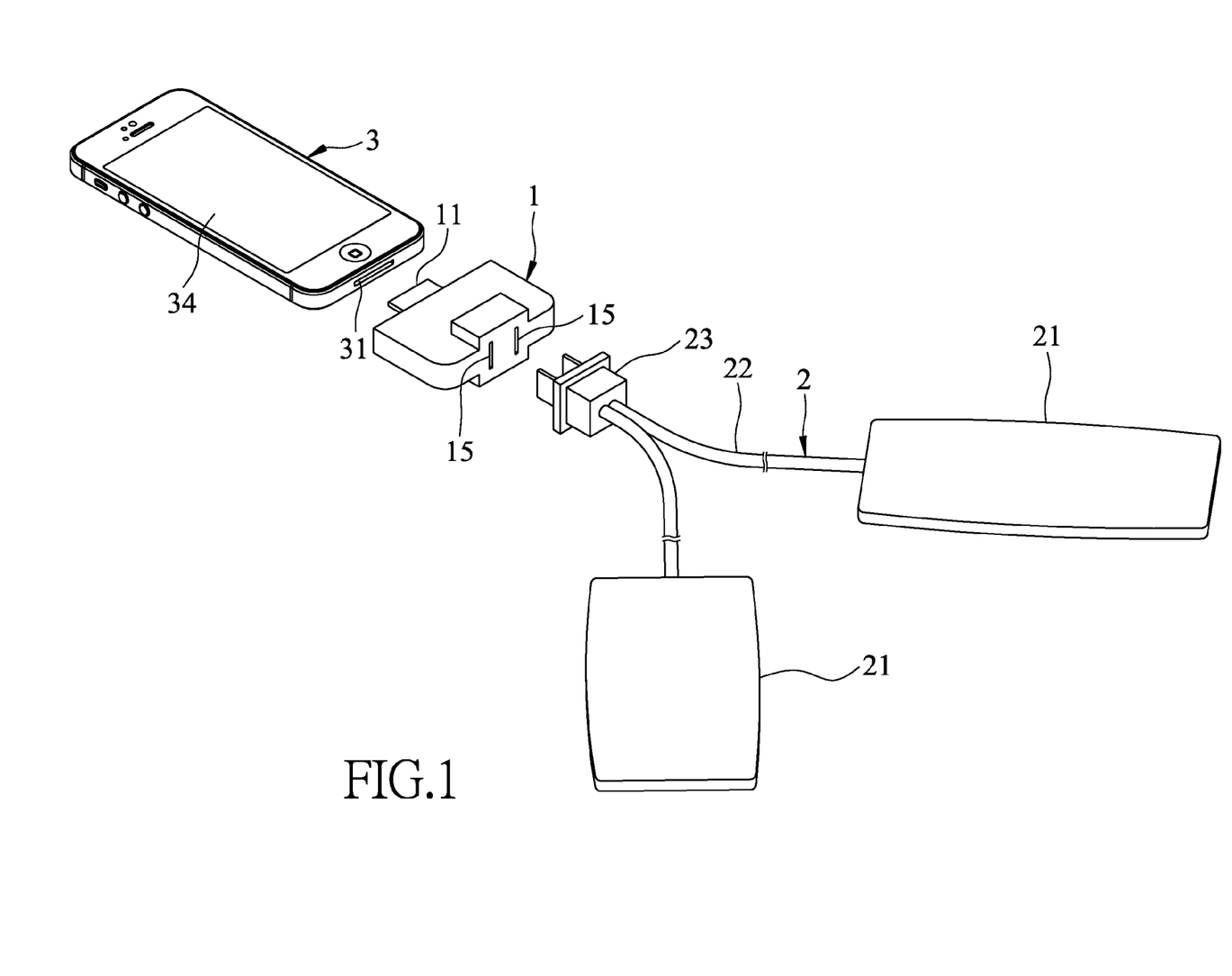
FIG. 1 is a perspective view showing a first preferred embodiment of a defibrillation system according to the present invention in a disassembled state.
Figure 2:
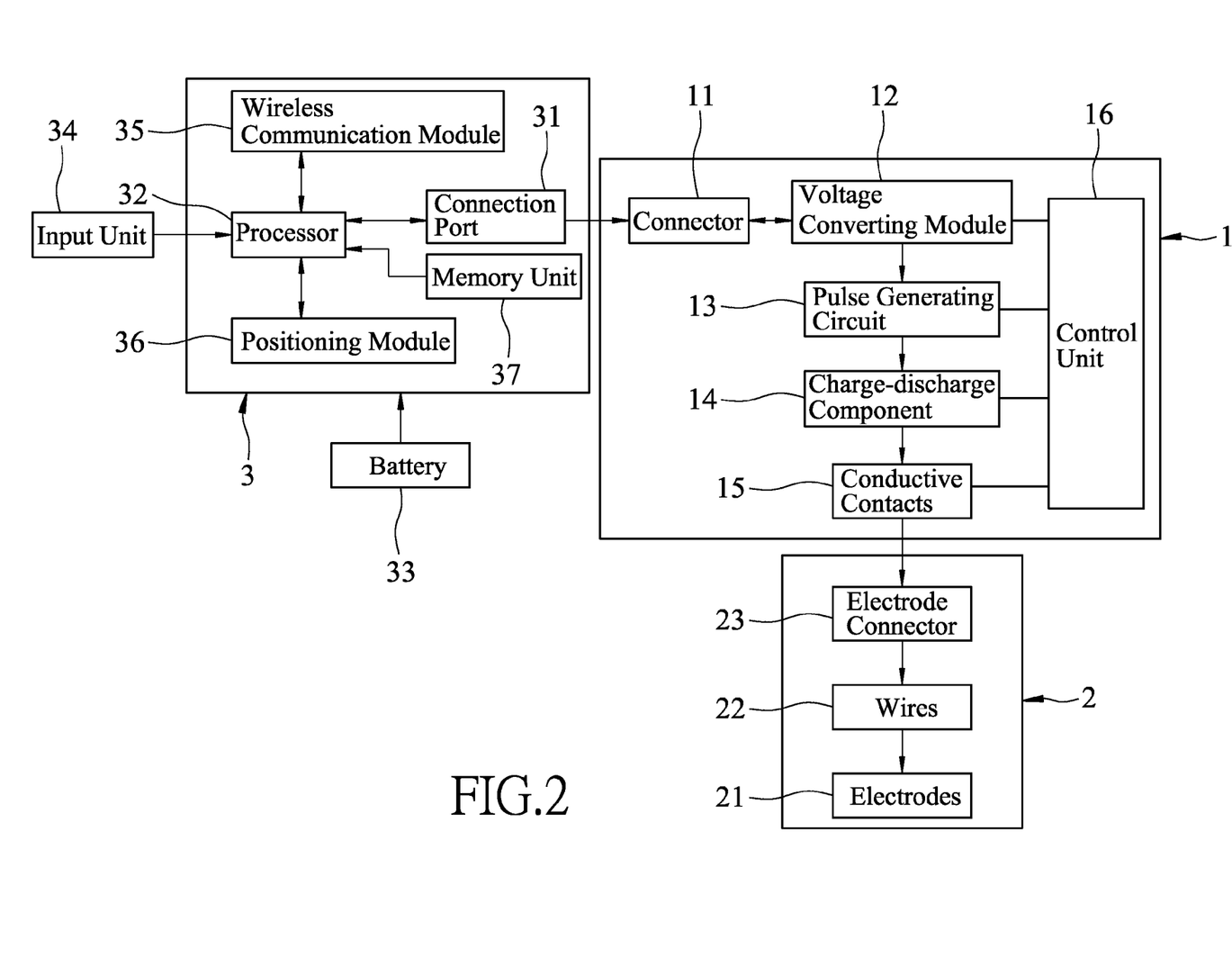
FIG. 2 is a block diagram of the first preferred embodiment.

The voltage transformer 1 includes a connector 11 coupled electrically and separably to the portable electronic device 3 for receiving a DC voltage therefrom, a voltage converting module 12 coupled electrically to the connector 11 and boosting the DC voltage received thereby from the connector 11, a pulse generating circuit 13 coupled electrically to the voltage converting module 12 and converting the DC voltage boosted by the voltage converting module 12 into a pulsating voltage signal, a charge-discharge component 14 (e.g., a supercapacitor) coupled electrically to the pulse generating circuit 13, a pair of conductive contacts 15 coupled electrically to the charge-discharge component 14, and a control unit 16 coupled to the charge-discharge component 14 and responsive to a discharge command received from the portable electronic device 3 through the connector 11 for controlling the charge-discharge component 14 to discharge.

The electrode set 2 includes a pair of electrodes 21 in a form of electrode pads for contacting the biological subject, a pair of wires 22 coupled electrically to the electrodes 21, and an electrode connector 23 coupled to the wires 22 and coupled separably and electrically to the conductive contacts 15 of the voltage transformer 1.

Figure 3:
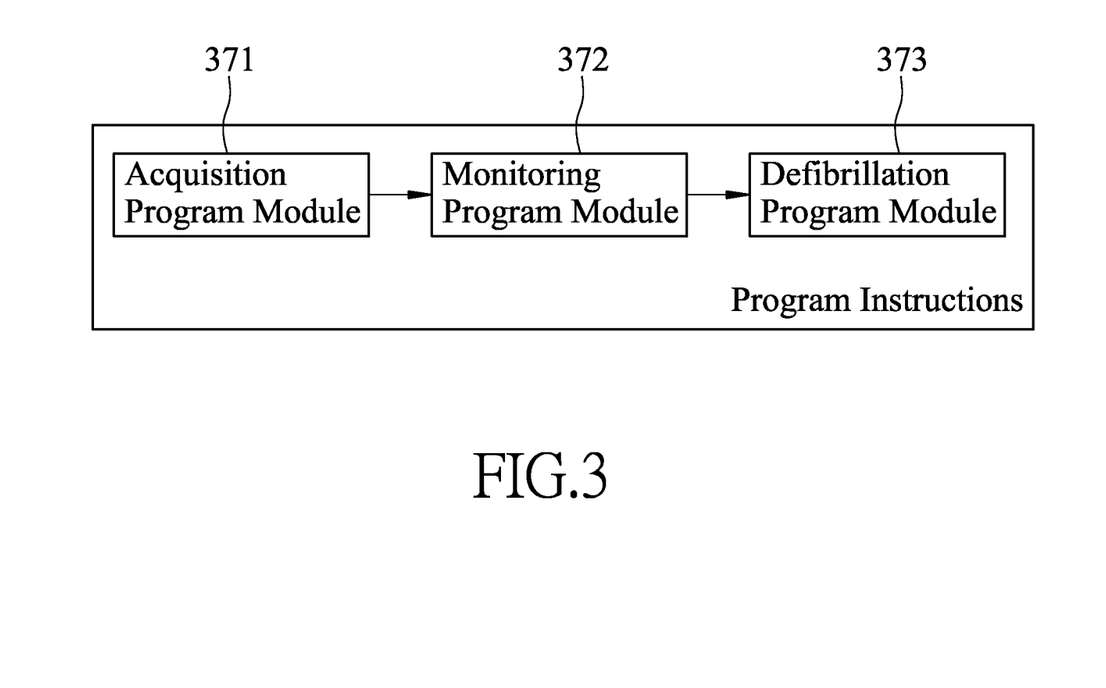
FIG. 3 is a block diagram showing functional blocks of program instructions stored in a memory unit of the first preferred embodiment.

In this embodiment, the portable electronic device 3 may be a smartphone or a tablet computer, and includes a connection port 31 coupled to the connector 11 of the voltage transformer 1, a processor 32, a battery 33, an input unit 34 (e.g., a touch screen) for input of an enable command, a wireless communication module 35 coupled electrically to the processor 32 and supporting mobile wireless communications, a positioning module 36 (e.g., global positioning system, GPS) coupled electrically to the processor 32 for detecting location of the portable electronic device 3, and a memory unit 37. The memory unit 37 stores program instructions including an acquisition program module 371 to enable the processor 32 to obtain an electro-cardiac signal of the biological subject, a monitoring program module 372 to enable the processor 32 to determine a shockable heart rhythm according to the electro-cardiac signal, and a defibrillation program module 373 to enable the processor 32 to perform defibrillation when the program instructions are executed by the processor 32. It should be noted that the program instructions that include the acquisition program module 371, the monitoring program module 372 and the defibrillation program module 373 may be obtained through application software (APP) installed in the portable electronic device 3.

Figure 4:
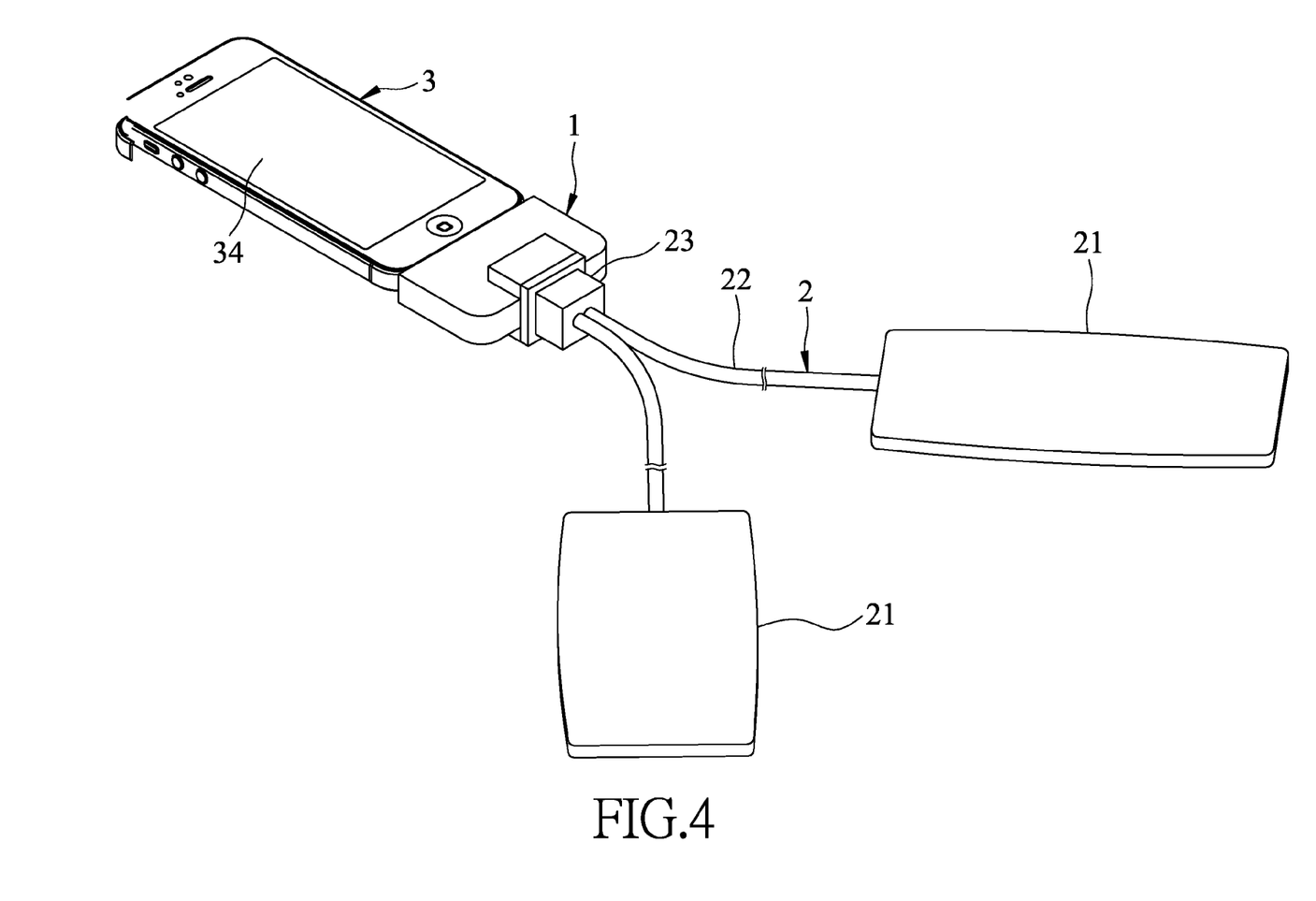
FIG. 4 is a perspective view showing the first preferred embodiment in an assembled state.
Figure 5:
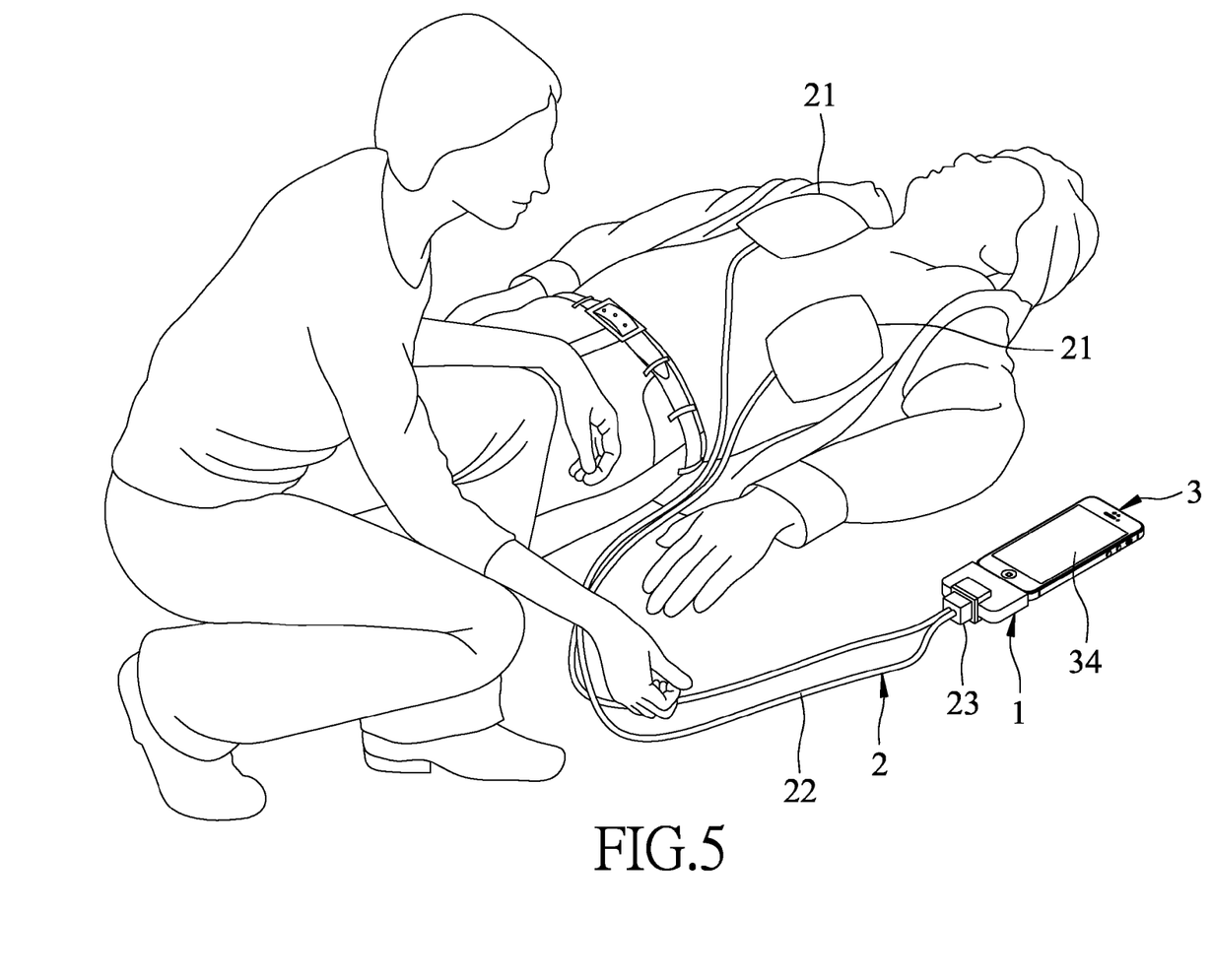
FIG. 5 is a schematic diagram showing the first preferred embodiment in a state of use.

Referring to FIGS. 2, 4 and 5, when using the first preferred embodiment, the connector 11 of the voltage transformer 1 is connected electrically to the connection port 31 of the portable electronic device 3, the electrodes 31 are attached respectively to the right-front chest portion (below the right clavicle) and the left chest portion (between the axilla and the ribs) of the biological subject, and the electrode connector 23 of the electrode set 2 is connected electrically to the conductive contacts 15 of the voltage transformer 1.

At this time, electricity of the battery 33 of the portable electronic device 3 is provided to the voltage transformer 1 through the connection port 31, so that the voltage converting module 12 converts and boosts the DC voltage received through the connection port 31, and the pulse generating circuit 13 converts the boosted DC voltage into the pulsating voltage signal for charging the charge-discharge component 14.

The program instructions of the APP, when executed by the processor 32, enable the processor 32 to obtain the electro-cardiac signal of the biological subject through the electrode set 3 according to the enable command, and to output a discharge command according to the electro-cardiac signal (i.e., the shockable heart rhythm) for delivering an electrical shock to the biological subject. In detail, the control unit 16 of the voltage transformer 1 receives the discharge command from the portable electronic device 3, and controls the charge-discharge component 14 of the voltage transformer 1 to discharge according to the discharge command, thereby delivering the electrical shock through the electrodes 21 of the electrode set 2.

Figure 6:
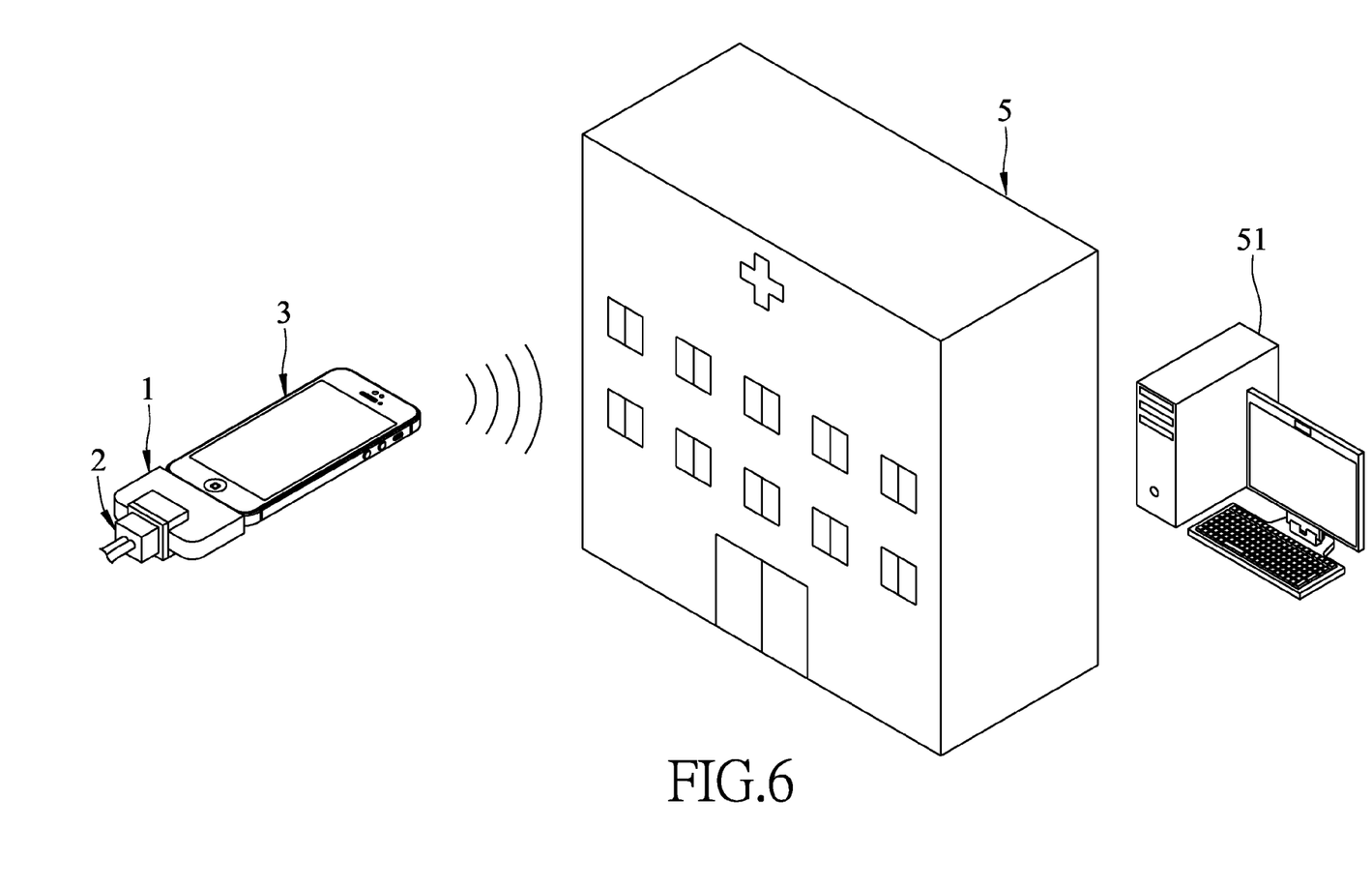
FIG. 6 is a schematic diagram showing the first preferred embodiment that is configured to transmit a distress message.

Referring to FIGS. 2 and 6, after the processor 32 outputs the discharge command, the positioning module 36 detects the location of the portable electronic device 3, and the program instructions of the APP will enable the processor 32 to find a medical facility 5 closest to the portable electronic device 3 according to the location detected by the positioning module 36, and to control the wireless communication module 35 to transmit a distress message that includes information of the location of the portable electronic device 3 to an equipment 51 in the medical facility found by the processor 32, so that medical personnel and an ambulance may arrive at the location accordingly.

Before the medical personnel arrives at the location, doctors or the medical personnel in the medical facility 5 may communicate with the people applying first-aid at the location through the wireless communication module 35 of the portable electronic device 3 for directing defibrillation, or may perform defibrillation through wireless control by use of the APP.

It should be noted that the electrical shock delivered by the present invention has a two-phase waveform with low energy and high efficiency, and has an output energy ranging between 150 joules and 200 joules. In general, a Li-ion battery has an output voltage ranging between 5V and 15V. The voltage converting module 12 may boost voltage supplied by the Li-ion battery to a desired voltage that may range between 1500V and 1800V, and the charge-discharge component 14 may store the boosted voltage therein for delivering the electrical shock.

Figure 7:
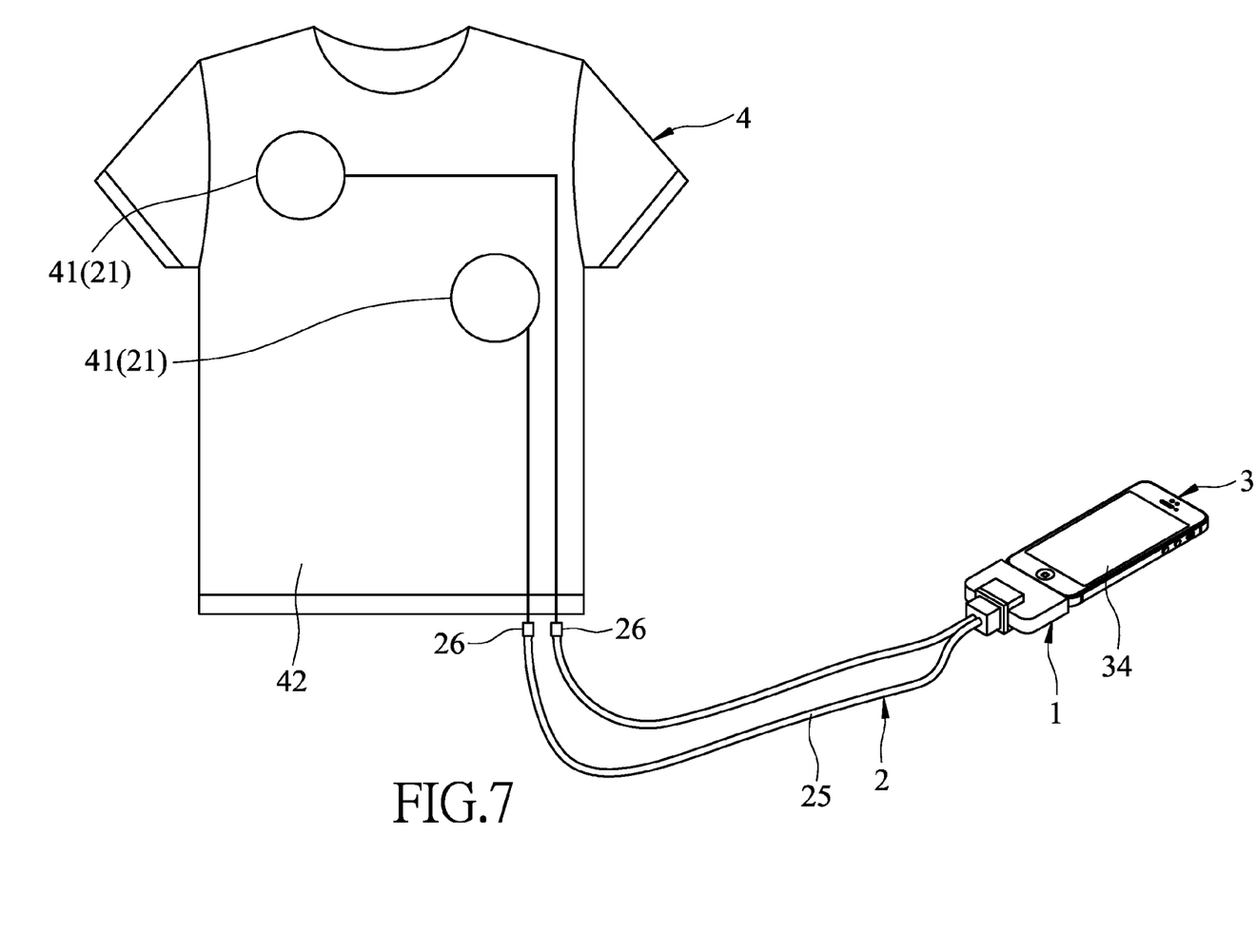
FIG. 7 is a schematic diagram showing a second preferred embodiment of the defibrillation system according to the present invention.

The electrode set 2 may be provided on a garment to be worn on the biological subject. Referring to FIG. 7, a second preferred embodiment of the defibrillation system according to the present invention is shown to be similar to the first preferred embodiment, and differs in that the second preferred embodiment further includes a shirt 4 provided with the electrode set 2.

In detail, the electrode set 2 includes a pair of electrodes 21 for delivering the electrical shock to the biological subject, a pair of wires 25 coupled electrically to the voltage transformer 1, and a pair of wire connectors 26 coupled respectively and electrically to the wires 25. The shirt 4 has a pair of first garment portions 41 that are made of electrically conductive fabric and that serve as the electrodes 21 of the electrode set 2, and a second garment portion 42 that is made of electrically insulating fabric, that is connected to the first garment portions 41, and that is thinner than the first garment portions 41, so that the first garment portions 41 are closer to the biological subject compared to the second garment portion 42 when the shirt 4 is worn on the biological subject. In this embodiment, the wire connectors 26 are coupled separably and electrically to the first garment portions 41. It should be noted that the first garment portions 41 are to be aligned with the right-front chest portion (below the right clavicle) and the left chest portion (between the axilla and the ribs) of the biological subject. VT/VF patients may wear the shirt 4 with a symbol indicating that the defibrillation system is provided therewith for informing the first-aid personnel to connect the wire connectors 26 to the first garment portions 41 when defibrillation is required to be performed, and additional electrode pads are not necessary.

Figure 8:
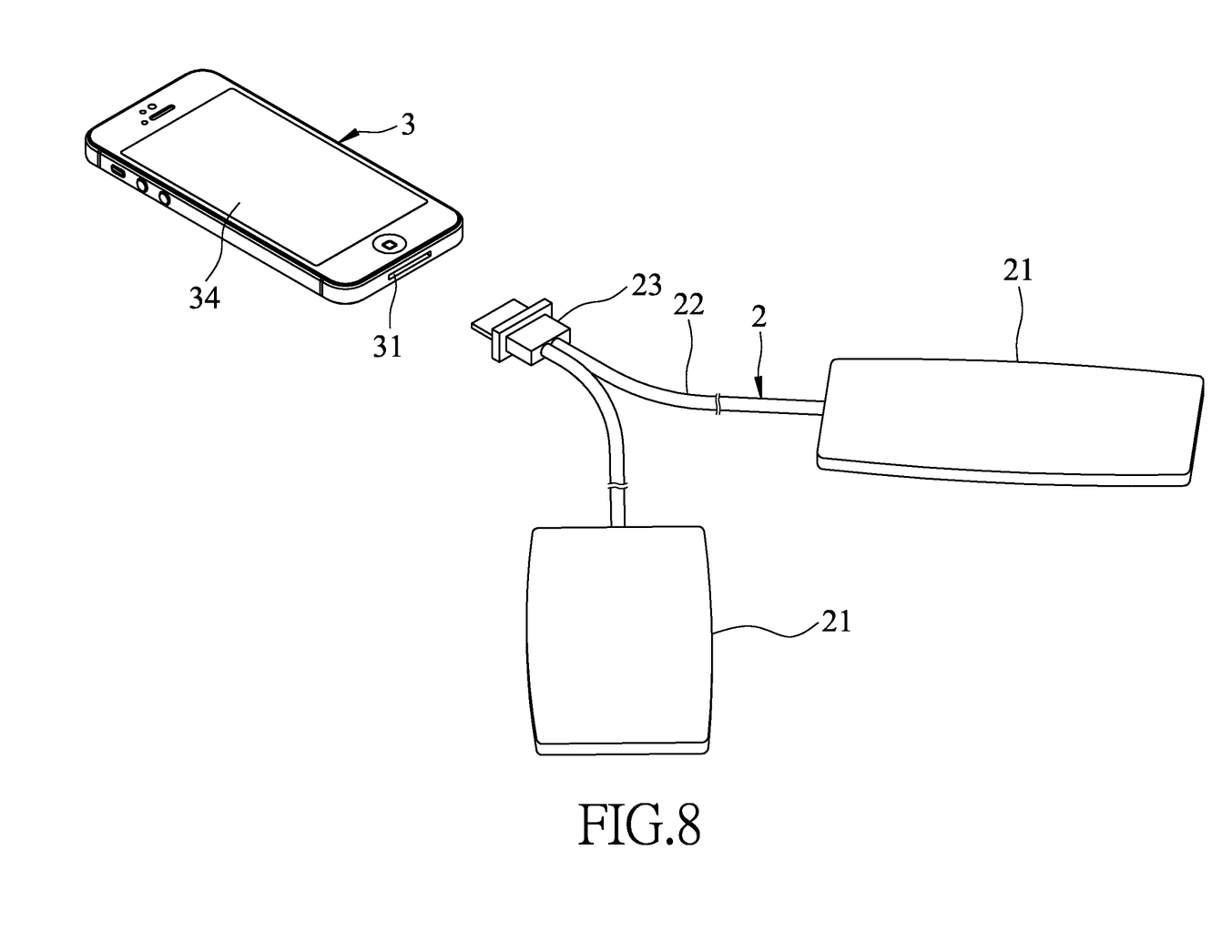
FIG. 8 is a perspective view showing a third preferred embodiment of the defibrillation system according to the present invention.
Figure 9:
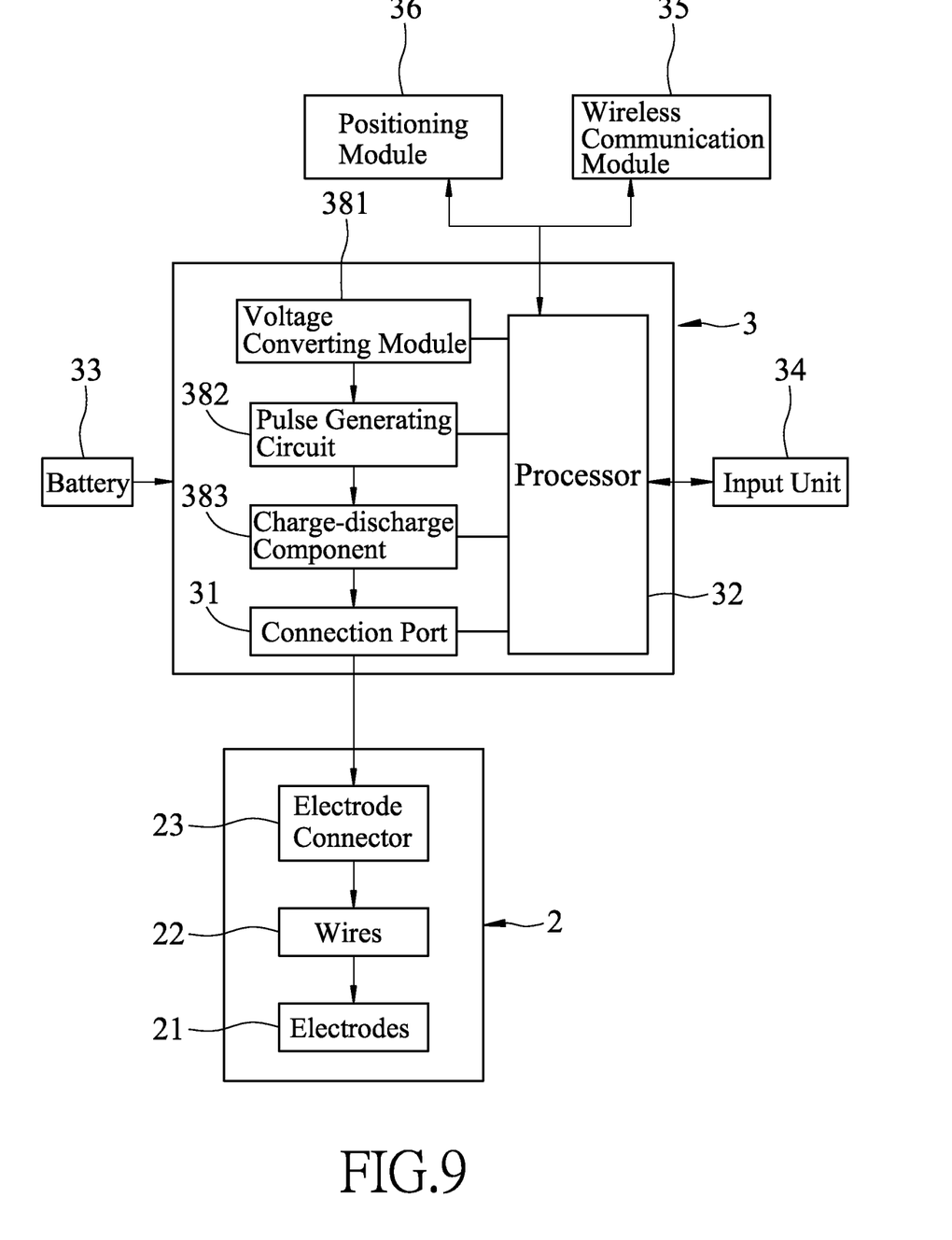
FIG. 9 is a block diagram of the third preferred embodiment.

Referring to FIGS. 8 and 9, a third preferred embodiment of the defibrillation system according to the present invention is shown to be similar to the first preferred embodiment, and differs in that the portable electronic device 3 includes a voltage converting module 381, a pulse generating circuit 382, and a charge-discharge component 383 instead of the voltage converting module 12, the pulse generating circuit 13, and the charge-discharge component 14 of the voltage transformer 1 of the first preferred embodiment, and the processor 32 directly controls the voltage converting module 381, the pulse generating circuit 382, and the charge-discharge component 383 without the control unit 16 of the first preferred embodiment.

Figure 10:
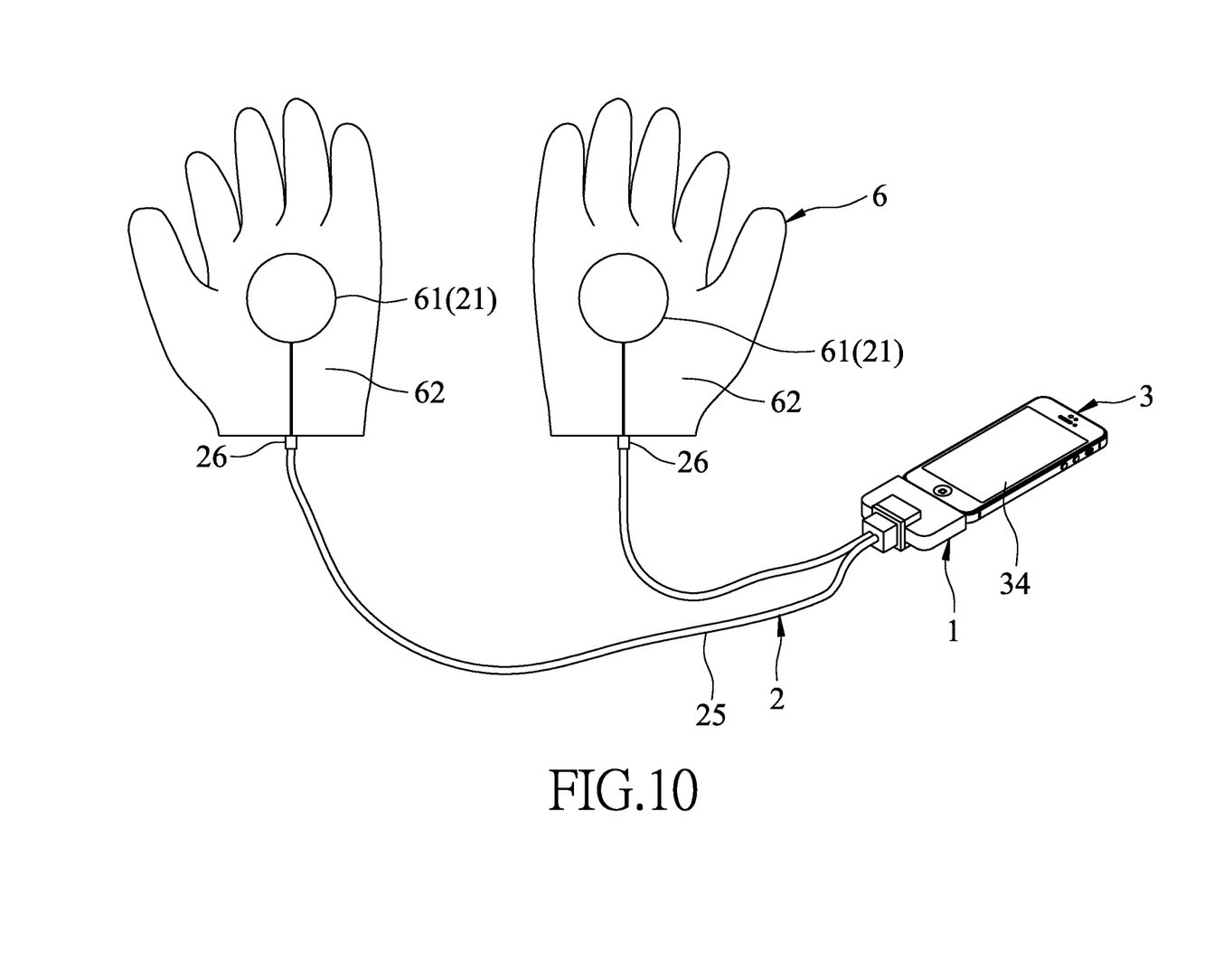
FIG. 10 is a schematic diagram showing a fourth preferred embodiment of the defibrillation system according to the present invention.

Referring to FIG. 10, a fourth preferred embodiment of the defibrillation system according to the present invention is shown to be similar to the second preferred embodiment, and differs in that the garment is a pair of gloves 6 that have first garment portions 61 made of electrically conductive fabric to serve as the electrodes 21, and a second garment portion 62 made of electrically insulating fabric.

The first-aid personnel may wear the gloves 6, and put the first garment portions 61 on the right-front chest portion (below the right clavicle) and the left chest portion (between the axilla and the ribs) of the biological subject respectively for performing defibrillation.

To sum up, the defibrillation system according to the present invention may use the APP to perform defibrillation through the portable electronic device 3 (e.g., smartphone or tablet computer), so as to promote popularity of the defibrillation system, and the survival rate of cardiac dysrhythmia. Furthermore, equipment cost may be reduced and more electrode sets 2 may be provided in more places.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A defibrillation system, comprising:
   an electrode set adapted to contact a biological subject;
   a portable electronic device that supports mobile wireless communications, that is coupled electrically and separably to said electrode set, and that includes a processor and a memory unit coupled to said processor, said memory unit storing program instructions which, when executed by said processor, enables said processor to
   obtain an electro-cardiac signal of the biological subject through said electrode set that contacts the biological subject, and
   output a discharge command according to the electro-cardiac signal for delivering an electrical shock to the biological subject, the electrical shock being delivered through said electrode set according to the discharge command; and
   a voltage transformer coupled electrically and separably to said portable electronic device, receiving the discharge command therefrom, and including:
   a voltage converting module coupled electrically to said portable electronic device for receiving a direct-current (DC) voltage therefrom and operable to boost the DC voltage;
   a pulse generating circuit coupled electrically to said voltage converting module and operable to convert the DC voltage boosted by said voltage converting module into a pulsating voltage signal;
   a charge-discharge component coupled electrically to said electrode set and said pulse generating circuit, configured to be charged by the pulsating voltage signal, and configured to discharge for delivering the electrical shock through said electrode set; and
   a control unit coupled to said charge-discharge component and responsive to the discharge command for controlling said charge-discharge component to discharge, thereby delivering the electrical shock through said electrode set.

2. The defibrillation system as claimed in claim 1, wherein said portable electronic device further includes a connection port, said voltage transformer further including:
   a connector coupled electrically and separably to said connection port for receiving the DC voltage and the discharge command therefrom, coupled to said voltage converting module for transmission of the DC voltage thereto, and coupled to said control unit for transmission of the discharge command thereto; and
   a pair of conductive contacts coupled to said charge-discharge component and said electrode set.

3. The defibrillation system as claimed in claim 1, further comprising a garment that is to be worn by the biological subject and that is provided with said electrode set.

4. The defibrillation system as claimed in claim 3, wherein said electrode set includes a pair of electrodes for delivering the electrical shock to the biological subject, said garment being a shirt having a pair of first garment portions that are made of electrically conductive fabric and that serve as said electrodes of said electrode set, and a second garment portion that is made of electrically insulating fabric, that is connected to said first garment portions, and that is thinner than said first garment portions.

5. The defibrillation device as claimed in claim 3, wherein said garment is a pair of gloves.

6. The defibrillation system as claimed in claim 1, wherein said portable electronic device further includes an input unit for input of an enable command, said program instructions, when executed by the processor, further enabling said processor to obtain the electro-cardiac signal of the biological subject through said electrode set according to the enable command.

7. The defibrillation system as claimed in claim 1, wherein said portable electronic device is one of a smartphone and a tablet computer.

8. A defibrillation system, comprising:
   an electrode set adapted to contact a biological subject;
   a portable electronic device that supports mobile wireless communications, that is coupled electrically and separably to said electrode set, and that includes:
   a processor;
   a memory unit coupled to said processor, said memory unit storing program instructions which, when executed by said processor, enables said processor to
   obtain an electro-cardiac signal of the biological subject through said electrode set that contacts the biological subject, and
   output a discharge command according to the electro-cardiac signal for delivering an electrical shock to the biological subject, the electrical shock being delivered through said electrode set according to the discharge command;
   a wireless communication module electrically coupled to said processor, said program instructions, when executed by said processor, further enabling said processor to control said wireless communication module to transmit a distress message after said processor outputs the discharge command; and
   a positioning module that is coupled to said processor and that is operable to detect location of said portable electronic device, the distress message transmitted by said wireless communication module including information of the location of said portable electronic device.

9. The defibrillation system as claimed in claim 8, wherein said program instructions, when executed by said processor, further enable said processor to find a medical facility closest to said portable electronic device according to the location detected by said positioning module, and to control said wireless communication module to transmit the distress message to the medical facility found by said processor.

10. A defibrillator electrode device adapted for use with a portable electronic device that supports mobile wireless communications and that includes a processor, said defibrillator electrode device comprising:
   an electrode set adapted to contact a biological subject;
   program instructions to be stored in the portable electronic device, said program instructions, when executed by the processor of the portable electronic device, enabling the processor to
   obtain an electro-cardiac signal of the biological subject through said electrode set that contacts the biological subject, and
   output a discharge command according to the electro-cardiac signal for delivering an electrical shock to the biological subject, the electrical shock being delivered through said electrode set according to the discharge command; and
   a voltage transformer to be coupled electrically and separably to the portable electronic device for receiving the discharge command therefrom, and including:
   a voltage converting module to be coupled electrically to the portable electronic device for receiving a direct-current (DC) voltage therefrom and operable to boost the DC voltage;
   a pulse generating circuit coupled electrically to said voltage converting module and operable to convert the DC voltage boosted by said voltage converting module into a pulsating voltage signal;
   a charge-discharge component coupled electrically to said electrode set and said pulse generating circuit, configured to be charged by the pulsating voltage signal, and configured to discharge for delivering the electrical shock through said electrode set; and
   a control unit coupled to said charge-discharge component and responsive to the discharge command for controlling said charge-discharge component to discharge, thereby delivering the electrical shock through said electrode set.

11. The defibrillator electrode device as claimed in claim 10, wherein said voltage transformer further includes:
   a connector to be coupled electrically and separably to the portable electronic device for receiving the DC voltage and the discharge command therefrom, coupled to said voltage converting module for transmission of the DC voltage thereto, and coupled to said control unit for transmission of the discharge command thereto; and
   a pair of conductive contacts coupled to said charge-discharge component and said electrode set.

12. The defibrillator electrode device as claimed in claim 10, further comprising a garment that is to be worn by the biological subject and that is provided with said electrode set.

13. The defibrillator electrode device as claimed in claim 12, wherein said electrode set includes a pair of electrodes for delivering the electrical shock to the biological subject, said garment being a shirt having a pair of first garment portions that are made of electrically conductive fabric and that serve as said electrodes of said electrode set, and a second garment portion that is made of electrically insulating fabric, that is connected to said first garment portions, and that is thinner than said first garment portions.

14. The defibrillator electrode device as claimed in claim 12, wherein said garment is a pair of gloves.

* * * * *